United States Patent
Bicho et al.

(10) Patent No.: US 10,450,700 B2
(45) Date of Patent: Oct. 22, 2019

(54) METHOD AND APPARATUS FOR CONTROLLING A CELLULOSIC PULP PROCESS

(71) Applicant: CANFOR PULP LTD, Burnaby (CA)

(72) Inventors: Paul Alexandre Bicho, Coquitlam (CA); Edward Robert Grant, Vancouver (CA); Pin-Wen Tsai, Surrey (CA); Najme Tavassoli, Vancouver (CA)

(73) Assignee: CANFOR PULP LTD., Burnaby, British Columbia (CA)

( * ) Notice: Subject to any disclaimer, the term of this patent is extended or adjusted under 35 U.S.C. 154(b) by 214 days.

(21) Appl. No.: 15/534,739

(22) PCT Filed: Dec. 12, 2014

(86) PCT No.: PCT/CA2014/000886
§ 371 (c)(1),
(2) Date: Jun. 9, 2017

(87) PCT Pub. No.: WO2016/090455
PCT Pub. Date: Jun. 16, 2016

(65) Prior Publication Data
US 2017/0342659 A1 Nov. 30, 2017

(51) Int. Cl.
*D21C 7/12* (2006.01)
*G01N 21/31* (2006.01)
(Continued)

(52) U.S. Cl.
CPC ............. *D21C 7/12* (2013.01); *D21C 3/00* (2013.01); *D21C 3/228* (2013.01); *D21C 9/00* (2013.01);
(Continued)

(58) Field of Classification Search
None
See application file for complete search history.

(56) References Cited

U.S. PATENT DOCUMENTS

| 4,013,506 | A | 3/1977 | Histed et al. |
| 4,222,064 | A | 9/1980 | Lodzinski |

(Continued)

FOREIGN PATENT DOCUMENTS

| CA | 2319074 A1 | 8/1999 |
| CA | 2403008 A1 | 2/2001 |

(Continued)

OTHER PUBLICATIONS

Definition of Polychromator, definitions.net, no date, [online], retrieved from the Internet,[retrieved Mar. 9, 2019], <URL: https://www.definitions.net/definition/polychrornator>. (Year: 2019).*

(Continued)

*Primary Examiner* — Dennis R Cordray (57) ABSTRACT

A method and apparatus for controlling a cellulosic pulp process for producing a pulp product having a desired pulp property is disclosed. The method involves illuminating an in-process portion of pulp using a first wavelength of light, and receiving a scattered light spectrum from the illuminated portion of pulp, the scattered light spectrum including spectral components that have been shifted in wavelength through interaction with a constituent of the illuminated portion of pulp. The method also involves filtering the scattered light spectrum to separate the spectral components, and identifying spectral features in the filtered scattered light spectrum that correspond to the pulp property. The method further involves generating a control signal for controlling the pulp process based on variations in the identified spectral features to cause the pulp property to fall within a desired range.

36 Claims, 5 Drawing Sheets

(51) Int. Cl.
*G01N 21/55* (2014.01)
*D21C 3/22* (2006.01)
*G01N 21/84* (2006.01)
*D21C 3/00* (2006.01)
*D21C 9/00* (2006.01)

(52) U.S. Cl.
CPC ............. *G01N 21/31* (2013.01); *G01N 21/55* (2013.01); *G01N 2021/8416* (2013.01)

(56) References Cited

U.S. PATENT DOCUMENTS

| | | | | |
|---|---|---|---|---|
| 5,420,682 | A | * | 5/1995 | Haggerty ............. G01J 3/28 162/263 |
| 5,486,915 | A | | 1/1996 | Jeffers et al. |
| 5,842,150 | A | | 11/1998 | Renberg et al. |
| 6,069,688 | A | | 5/2000 | Millar et al. |
| 6,744,500 | B2 | | 6/2004 | Bradbury et al. |
| 2001/0017195 | A1 | | 8/2001 | Trung et al. |
| 2005/0088653 | A1 | * | 4/2005 | Coates ............. G01N 21/85 356/419 |
| 2006/0196622 | A1 | | 9/2006 | Trung et al. |
| 2012/0031577 | A1 | | 2/2012 | Banks et al. |

FOREIGN PATENT DOCUMENTS

| | | |
|---|---|---|
| CA | 2392292 A1 | 7/2001 |
| EP | 0946816 B1 | 9/2002 |
| WO | 9939044 A1 | 8/1999 |
| WO | 0165237 A1 | 9/2001 |
| WO | 2006007683 A1 | 1/2006 |

OTHER PUBLICATIONS

International Search Report issued by the Canadian Intellectual Property Office in connection with International Patent Applicaiton No. PCT/CA2014/000886, dated Jul. 28, 2015, 4 pages.

Written Opinion of the International Searching Authority issued by the Canadian Intellectual Property Office in connection with International Patent Application No. PCT/CA2014/000886, dated Jul. 28, 2015, 5 pages.

D. Chen et al., High-throughput prediction of physical and mechanical properties of paper from Raman chemometric analysis of pulp fibres, Can. J. For. Res. 41:2100-2113, 2011, published by NRC Research Press.

N. Tavassoli et al. "Template-oriented genetic algorithm (TOGA) feature selection of analyte wavelets in the Raman spectrum of a complex mixture", Department of Chemistry, University of British Columbia, Vancouver, Bc V6T 1Z1, Canada and State Key Laboratory of Precision Measuring Technology and Instruments, Tianjin University, Tianjin 300072, China.

Karlsson, Lennart, European Patent Office, Extended European Search Report, in connection with related European Patent Application No. 14908068 dated Jul. 6, 2018, 6 pages.

International Search Report issued by the Canadian Intellectual Property Office in connection with International Patent Application No. PCT/CA2014/000886, dated Jul. 28, 2015, 4 pages.

* cited by examiner

METHOD AND APPARATUS FOR CONTROLLING A CELLULOSIC PULP PROCESS

BACKGROUND OF THE INVENTION

1. Field of Invention

This invention relates generally to cellulosic pulp processes and more particularly to controlling a pulp processes for producing a pulp product having a desired pulp property.

2. Description of Related Art

The processing of wood chips into a pulp product involves multiple processing stages, some of which may have a duration of many hours. Accordingly, in a pulp processing plant there may be a substantial volume of pulp in process at any given time. The processing of pulp may be influenced by many factors, some of which may cause the value of the final pulp product to be reduced or rendered worthless. In some cases pulp properties that cause reduced value are only apparent in the final product and wastage of partially processed pulp, energy, and additive chemicals may result. There remains a need for methods and apparatus for controlling properties of the pulp product while the pulp is in-process.

SUMMARY OF THE INVENTION

In accordance with one disclosed aspect there is provided a method for controlling a cellulosic pulp process for producing a pulp product having a desired pulp property. The method involves illuminating an in-process portion of pulp using a first wavelength of light, and receiving a scattered light spectrum from the illuminated portion of pulp, the scattered light spectrum including spectral components that have been shifted in wavelength through interaction with a constituent of the illuminated portion of pulp. The method also involves filtering the scattered light spectrum to separate the spectral components, and identifying spectral features in the filtered scattered light spectrum that correspond to the pulp property. The method further involves generating a control signal for controlling the pulp process based on variations in the identified spectral features to cause the pulp property to fall within a desired range.

In accordance with another aspect of the invention there is provided an apparatus for controlling a cellulosic pulp process for producing a pulp product having a desired pulp property. The apparatus includes an illumination source operable to produce a first wavelength of light for illuminating an in-process portion of pulp. The apparatus also includes a receiver operable to receive a scattered light spectrum from the illuminated portion of pulp, the scattered light spectrum including spectral components that have been shifted in wavelength through interaction with a constituent of the illuminated portion of pulp. The receiver is also operable to filter the scattered light spectrum to separate the spectral components. The apparatus also includes a processor circuit operably configured to identify spectral features in the filtered scattered light spectrum that correspond to the pulp property, and to generate a control signal for controlling the pulp process based on variations in the identified spectral features to cause the pulp property to fall within a desired range.

Other aspects and features of the present invention will become apparent to those ordinarily skilled in the art upon review of the following description of specific embodiments of the invention in conjunction with the accompanying figures.

DETAILED DESCRIPTION

Pulp Processing Plant

Figure 1:
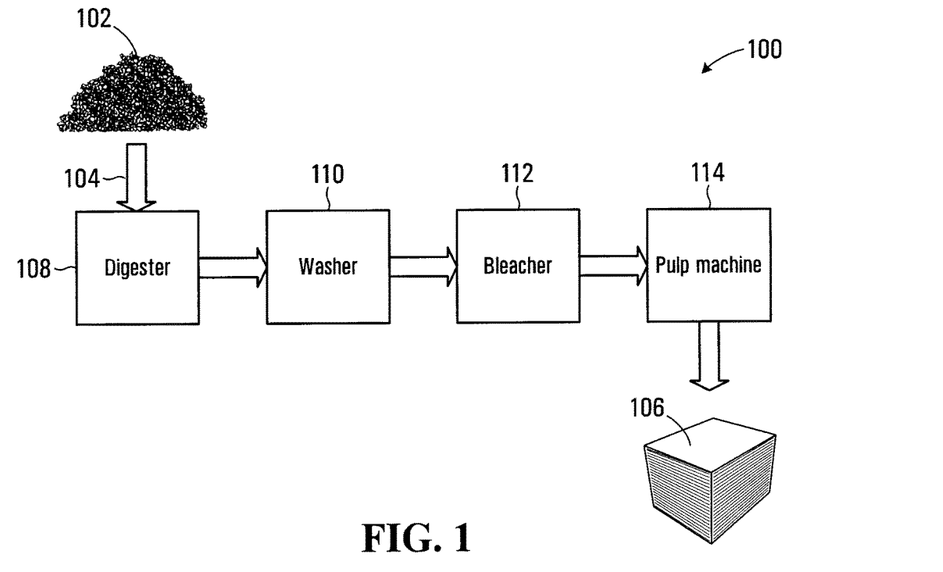
FIG. 1 is a schematic diagram of a pulp processing plant.

Referring to FIG. 1, a schematic view of a pulp processing plant is shown generally at 100. The pulp processing plant 100 receives a feed of wood chips 102 at an inlet 104. The end product may be a plurality of dried pulp mats in a pulp bale 106, which may be further processed to make various paper products.

The wood chips 102 received at the inlet 104 are fed into a digester 108 and saturated with water and cooking liquors. The cooking liquor is primarily white liquor, which is an alkaline solution including sodium hydroxide and sodium sulfide. The cooking liquors may also include some recovered sodium hydroxide and sodium sulfide from black liquor, which is a waste product of the process. In the digester 108 the cooking liquors penetrate the capillary structure of the wood chips and the materials are heated for several hours at high pressure and at temperatures of above 170° C. to degrade lignin and hemicellulose producing a pulp. Once cooked in the digester 108, the pulp is subjected to a blowing process by reducing the pressure in the digester to atmospheric pressure. The blowing process results in wood chips in the pulp being fluffed to form a brown pulp which is screened to remove knots, shives, and other debris and then passed to the washer 110. In the washer 110, black liquor is separated from cellulose fibers and the washed pulp is fed into a bleach plant 112. The bleach plant 112 may have several bleaching stages in which chemicals such as chlorine dioxide, hydrogen peroxide, and oxygen are used to whiten the pulp to a desired degree. The bleached pulp is then passed to the pulp machine 114, where it is dried, and pressed into pulp mats and accumulated in pulp bales 106.

In pulp production, it is generally desirable to remove a substantial portion of the lignin from the pulp, since lignin is responsible for yellowing of pulp products with age. High-quality paper is usually produced using pulp mats from which most of the lignin has been removed during processing. Lignin is removed from the pulp in the separated black liquor. The black liquor may be further processed to provide a fuel source for producing energy for running the process and to recover chemicals for re-use in the process.

The pulp processing plant 100 shown in FIG. 1 represents only one possible implementation of a pulp process using the Kraft process. In practice, pulp may be processed into paper products using a processing plant that differs in some or many aspects from the plant shown in FIG. 1 such as a sulfite pulp process or a thermomechanical pulping process. Alternatively, wood chips 102 may be processed to produce a pulp suitable for spinning into synthetic fibers such as Rayon.

Pulp Process Control Apparatus

Figure 2:
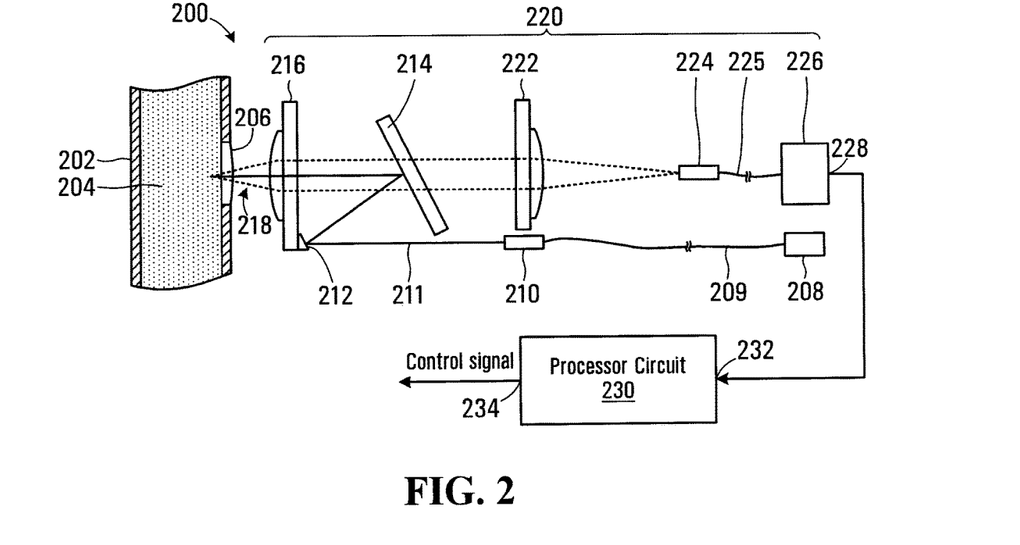
FIG. 2 is a schematic diagram of an apparatus for controlling a cellulosic pulp process in accordance with one embodiment of the invention.

Referring to FIG. 2, an apparatus for controlling a cellulosic pulp process in accordance with one embodiment of the invention is shown generally at 200. A conduit 202 carries a flow of pulp material 204 and may be located in or between any of the various processing stages of the pulp processing plant 100 shown in FIG. 1. The flow of pulp material may be an in-process pulp suspension having a pulp consistency of about 3%-6%. However in other embodiments the consistency of the pulp flow may be higher or the apparatus may be used to control the process based on measurements made of pulp sheets produced by the pulp machine 114 shown in FIG. 1.

The conduit 202 includes a window 206 for providing measurement access to the pulp material 204. The conduit 202 may be disposed inline between the digester 108 and the washer 110, within the bleach plant 112 or between the bleach plant and the pulp machine 114 or at other locations within the pulp processing plant 100. In other embodiments, the apparatus 200 may be located within or after the pulp machine 114 where the pulp material is in an accessible form (for example when the pulp is being processed into a pulp mat in the pulp machine 114), in which case the window 206 and conduit 202 may not be required.

The apparatus 200 includes an illumination source 208 that produces a first wavelength of light, which is coupled into an optical fiber 209 for transmission to an illumination coupler 210. The illumination coupler 210 couples the light from the optical fiber 209 into an illumination beam 211, which is directed via a turning mirror 212 and a dichroic filter 214 through a lens 216 to impinge on the flow of pulp material 204. The dichroic filter 214 is configured to reflect light at the first wavelength associated with the illumination beam 211. In one embodiment the illumination source 208 may have a wavelength in the range of 200-1000 nanometers. As an example the illumination source 208 may be a diode laser, which are available at common wavelengths such as 532, 633, and or 785 nanometers. The illumination beam 211 impinging on the flow of pulp material 204 produces a scattered light spectrum 218 (shown in broken lines in FIG. 2).

The apparatus 200 also includes a receiver 220 for receiving and conditioning the scattered light spectrum 218. The scattered light spectrum 218 includes spectral components that have been shifted in wavelength through interaction with constituents of the pulp material 204. The shift in wavelength is generally referred to as a Raman shift, and occurs when the illumination beam 211 interacts with constituents of the pulp material 204 causing photons in the beam of light to be shifted up or down in energy. The energy shift may be detected as a wavelength change in components of the scattered light spectrum 218 with respect to the first wavelength of illumination beam 211. The energy shift provides information associated with vibrational modes of constituent molecules of the pulp material 204. The wavelength shifted components may thus be associated with different constituents and may be used to determine proportions of the constituents in the pulp material.

In the embodiment shown the receiver 220 includes the lens 216, the dichroic filter 214, a lens 222, a fiber coupler 224 and optical fiber 225, and a spectrographic detector 226. The lens 216 collects the scattered light spectrum 218 and directs the light toward the dichroic filter 214, which filters the scattered light spectrum to separate wavelength shifted spectral components from spectral components at the wavelength of the illumination beam 211. The dichroic filter 214 is configured to transmit wavelengths other than the first wavelength associated with the illumination beam 211, which as noted above is reflected by the dichroic filter. Raman shifted spectral components are generally very weak and the scattered light spectrum 218 will usually be dominated by Rayleigh scattered light at the wavelength of the illumination beam 211. The separated wavelength shifted spectral components are collected by the lens 222 and coupled through the fiber coupler 224 into the optical fiber 225 for transmission to the spectrographic detector 226. The spectrographic detector 226 produces a spectral signal at an output 228.

In one embodiment the spectrographic detector 226 may include a diffraction grating that disperses the collected light spectrum into a plurality of spatially separated spectral components. Spectral components of longer wavelength are diffracted by the grating to a greater extent than spectral components having shorter wavelengths, thus providing a spatial separation of spectral components as a function of wavelength. The spectrographic detector 226 may use a charge coupled device (CCD) image sensor to conveniently image the spatially separated spectral components. The CCD image sensor includes a plurality of sensor elements in an array and produces a digital spectral data signal including a plurality of values representing an intensity of light impinging on each sensor element. The intensity of the spectral components may be determined by averaging data values associated with columns of sensor elements, each column effectively providing a sample corresponding to a particular wavelength range.

The apparatus 200 also includes a processor circuit 230. The processor circuit 230 includes an input 232 for receiving the spectral data signal produced at the output 228 of the spectrographic detector 226 and is configured to identify spectral features in the filtered scattered light spectrum 218 that correspond to the desired pulp property. A process for identifying the spectral features is described later herein. The processor circuit 230 is also configured to generate a control signal at an output 234 for controlling the pulp process based on variations in the identified spectral features to cause the pulp property to fall within a desired range.

Wood pulp includes lignin, which has a strong florescence across all visible wavelengths (i.e. in the range of about 350 nm to 900 nm). The scattered light spectrum 218 may thus be dominated by lignin florescence components making extraction of the Ramam shifted spectral components associated with vibration modes of constituents more difficult. In general, the proportion of lignin in the pulp reduces as the pulp material is processed through the pulp processing plant 100 shown in FIG. 1. In the bleach plant 112, lignin content is usually significantly reduced in the later bleaching stages and the apparatus 200 may be advantageously located to monitor the pulp material in one of these later bleaching stages. The Raman shifted spectral components in the scattered light spectrum 218 are more readily detected and processed when there is less background florescence from the pulp material and lower lignin content is a significant contributor toward background florescence.

In one embodiment the desired pulp property may be related to the tensile strength of the pulp product. Tensile strength is an important property for many secondary manufacturers who will process the pulp mats in the pulp bale 106 to produce products such as bathroom tissue, paper towel, and other paper products. If the pulp material is processed too aggressively or for too long in the digester 108, washer 110, or bleach plant 112 the cellulose fibers may become denatured and/or unraveled, thus lowering the tensile strength of products made from the pulp. Additionally hemicellulose is associated with bonding between cellulose fibers, and removal of hemicellulose during pulp processing may also have an impact on tensile strength and other properties.

In other processing embodiments such as the production of synthetic fiber from cellulose pulp materials, the viscosity of the pulp is an important pulp property and it may be desirable to provide for in-process control of the pulp viscosity.

Processor Circuit

Figure 3:
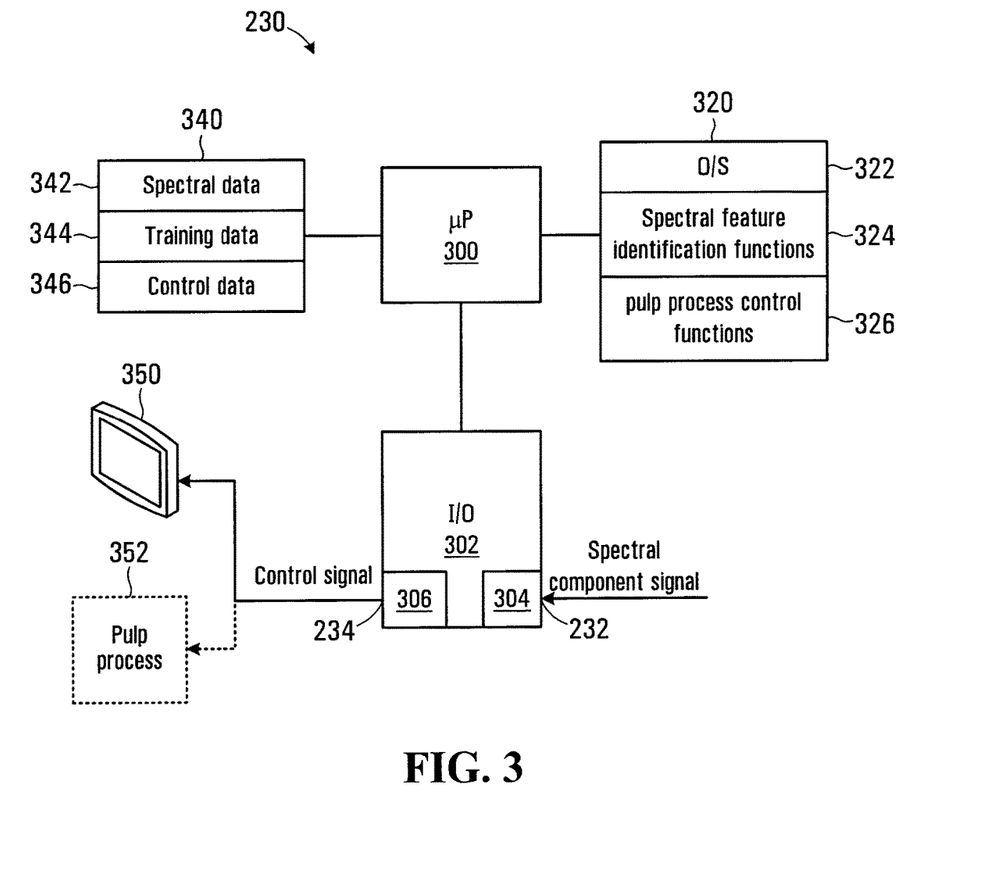
FIG. 3 is a schematic diagram of a processor circuit used in the apparatus shown in FIG. 2.

A schematic diagram of a processor circuit for implementing the processor circuit 230 is shown in FIG. 3. Referring to FIG. 3, the processor circuit 230 includes a microprocessor 300, an input output port (I/O) 302, a program memory 320, and a variable memory 340, all of which are in communication with the microprocessor 300.

Program codes for directing the microprocessor 300 to carry out various functions are stored in the program memory 320, which may be implemented as a random access memory (RAM), flash memory, and/or a hard disk drive (HDD), or a combination thereof. Program codes may be received from a host system or other connected system and loaded into the program memory 320. The program memory 320 includes a first block of program codes 322 for directing the microprocessor 300 to perform operating system functions, a second block of program codes 324 for directing the microprocessor 300 to perform spectral feature identification functions, and a third block of program codes 326 for directing the microprocessor 300 to perform pulp process control functions.

The I/O 302 includes a plurality interfaces including an interface 304 providing the input 232 (shown in FIG. 2) for receiving the spectral data signal from the output 228 of the spectrographic detector 226. The interface 304 may be a universal serial bus (USB) or other data interface. Alternatively, in some embodiments an analog signal may be produced by the spectrographic detector 226 and the interface 304 may include an analog to digital converter for converting the analog signal into a digital spectral representation. The I/O 302 also includes an interface 306 providing the output 234 (shown in FIG. 2) for producing the control signal. In one embodiment the control signal produced at the output 310 is used to cause a display 350 to display control information to provide an operator of the pulp processing plant 100 with necessary information for controlling the pulp process. In other embodiments, the control signal produced at the output 234 is generated and is used alone or in conjunction with signals representing other process parameters to control one or more pulp process stages 352. The control signal at the output 234 may be used in both feed-forward control and feed-backward control strategies.

The variable memory 340 includes a plurality of storage locations including a spectral data location 342 for storing data representing the scattered light spectrum produced by the spectrographic detector 226, a training data location 344 for storing results of a training analysis generated using a process described below, and a control data location 346 for storing data related to control of the pulp processing plant 100. The variable memory 340 may be implemented in random access memory, for example.

Training Process

Figure 4:
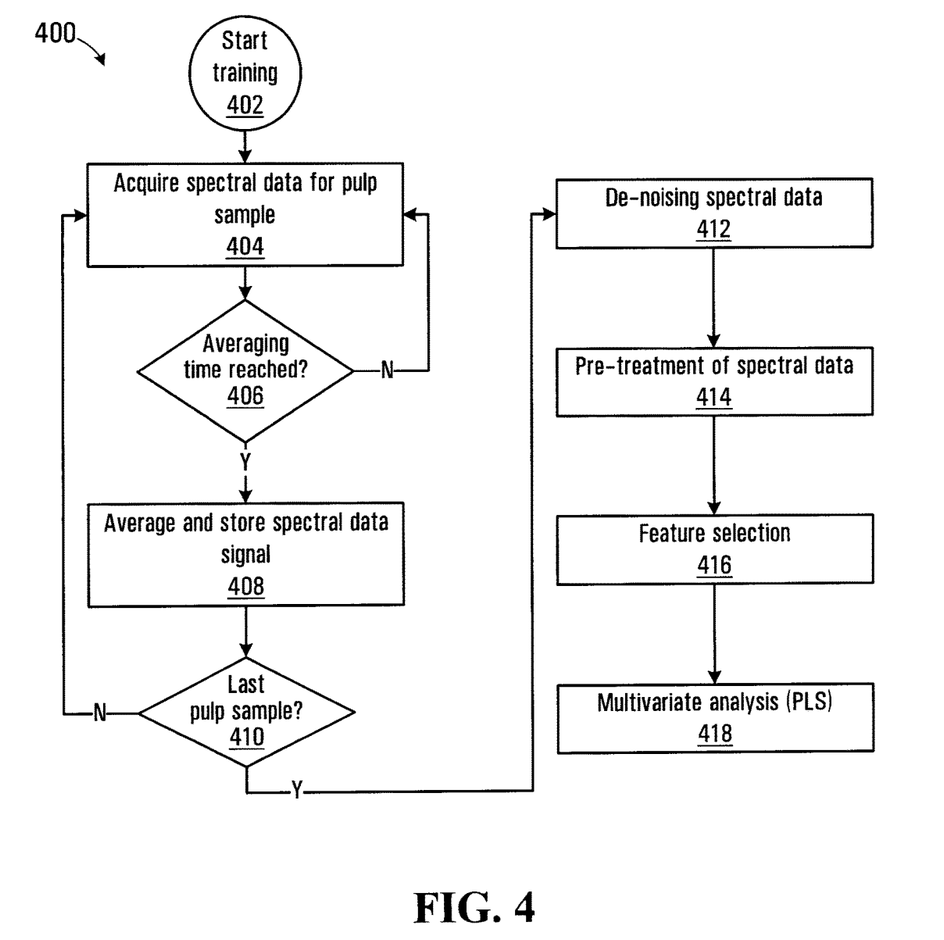
FIG. 4 is a process flowchart depicting blocks of codes for directing the processor circuit to implement a training process.

Referring to FIG. 4 a flowchart depicting blocks of code for directing the processor circuit 230 to perform a training process for identifying spectral features in accordance with one embodiment of the invention is shown at 400 in FIG. 4. In the following description, the training process 400 is described for a diffraction grating filter and a CCD based spectrographic detector 226. The spectral data signal at the output 228 of the CCD would thus be in the form of a digital data signal including data values representing a spectral intensity impinging on each element of the CCD. The blocks of the process 400 generally represent codes that may be read from the program codes 324 in the program memory 320 for directing the microprocessor 300 to perform functions related to identifying spectral features. The actual code to implement each block may be written in any suitable program language, such as C, C++, Java, assembly code, or in MATLAB® high-level numerical computation language, for example. In this embodiment, the training process 400 precedes the process for measurement of the desired pulp property for controlling the pulp processing plant 100.

The process 400 begins at block 402, which directs the microprocessor 300 to load and execute the spectral feature identification program codes 324 from the program memory 320. Block 404 then directs the microprocessor 300 to cause the I/O 302 to acquire spectral data at the input 232 of the interface 304 for a first pulp sample. In general the training process relies on receiving spectral data for a plurality of different pulp samples to provide for reliable predictions of pulp properties. Block 406 directs the microprocessor 300 to determine whether an averaging time for the pulp sample has been reached. In this embodiment spectral data for each pulp sample is acquired and averaged over a period of time as the pulp sample flows through the conduit 202. The averaging time may be predetermined and may be selected to be about 10 seconds. Accordingly, if at block 406 the averaging time has not yet been reached, the microprocessor 300 is directed back to block 404 and a further sample of the spectral data is acquired.

If at block 406, the averaging time has been reached, the microprocessor 300 is directed to block 408, which directs the microprocessor to average and store the spectral data in the spectral data memory location 342 of the variable memory 340. The acquired spectral data signals are thus combined to produce single set of averaged spectral data values representing the filtered scattered light spectrum 218.

Figure 6:
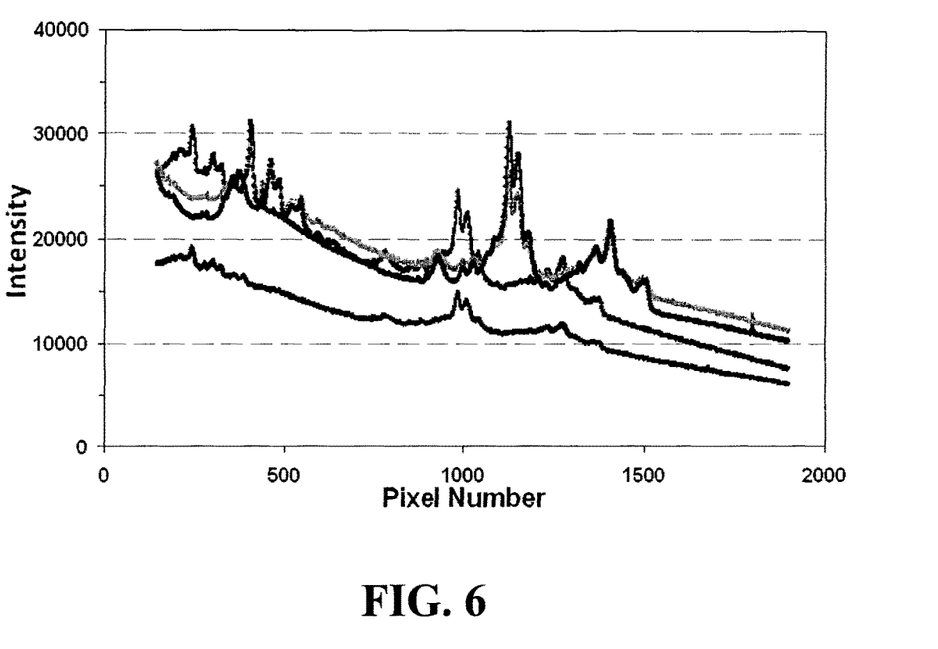
FIG. 6 is a graphical depiction of unprocessed spectra of 4 different chemical pulps.

Block 410 then directs the microprocessor 300 to determine whether there are further pulp samples to be processed, in which case the microprocessor is directed back to block 404 and spectral data for the next pulp sample is acquired. Blocks 404 to 408 are then repeated for each subsequent pulp sample. Examples of unprocessed spectra of 4 different chemical pulps are shown in FIG. 6.

In some embodiments the training process may involve acquiring spectral data for a plurality of pulp samples, which are randomly separated into a training plurality of spectral data and a classification plurality of spectral data for evaluating the effectiveness of the training process. Clearly, if training process effectiveness is evaluated using data used to generate the analysis then the resulting prediction may be unreliable. Testing the effectiveness of the training analysis using the classification plurality of spectral data is therefore expected to provide improved more reliable prediction results.

If at block 410, the last pulp sample has been processed, the microprocessor 300 is directed to block 412. If the last pulp sample has not yet been processed the microprocessor 300 is directed back to block 404.

Block 412 directs the microprocessor 300 to de-noise the spectral data, which may involve processes such as the application of a discrete wavelet transform or other multi-resolution filter bank to factor the response into components associated with various sources of noise. The noise sources may include (1) background noise due to due to for example, Rayleigh scattered light, fluorescence or a fixed-pattern response of the detector, (2) noise arising from thermal and statistical fluctuations in each detection channel, and/or (3) a spectral signal of molecular vibrations produced by the Raman effect (inelastic light scattering).

In other embodiments a neural network analysis may be used to implement block 412.

Block 414 then directs the microprocessor 300 to perform pre-treatment of the spectral data for calibration purposes, which generally involves preparing spectra for further analysis (such as feature selection) prior to modeling. In one embodiment pre-treatment may refer to a first-derivative or second-derivative transformation of the de-noised data, or refer to coefficients of the discrete wavelet transform (DWT) process, which decomposes the spectral data into spectral components of varying local frequency at successive wavelength positions in the averaged spectral data. In other embodiments the pre-treatment may involve implementing a template oriented genetic algorithm (TOGA), which uses a variance template to select a small number of wavelet components optimally correlated with a targeted property of a calibration set with the particular aim of reducing the dimensionality of the dataset to avoid over-fitting. Block 416 then directs the microprocessor 300 to perform a feature selection process whereby those spectral features that correlate with the pulp properties (thus improving the model's predictive capabilities) are selected while other spectral features are excluded from further analysis. This can be done by running an initial calibration model which includes all data and noting which spectral features contribute to the model's accuracy. The TOGA process excludes features that do not reduce the error of prediction More specifically, block 418 directs the microprocessor 300 to build a multivariate classification model for determining the effectiveness of the initially selected set of DWT spectral components in predicting the desired pulp property. In one embodiment a partial least squares (PLS) regression is implemented. The PLS regression uses the reserved classification plurality of spectral data for evaluating the effectiveness of the training process. The PLS regression may result in generation of a mean square error of prediction (RMSEP) value that may be used on its own or in combination with other error prediction values to generate an effectiveness value for the selected set of DWT spectral components.

Generating Control Signal

Figure 5:
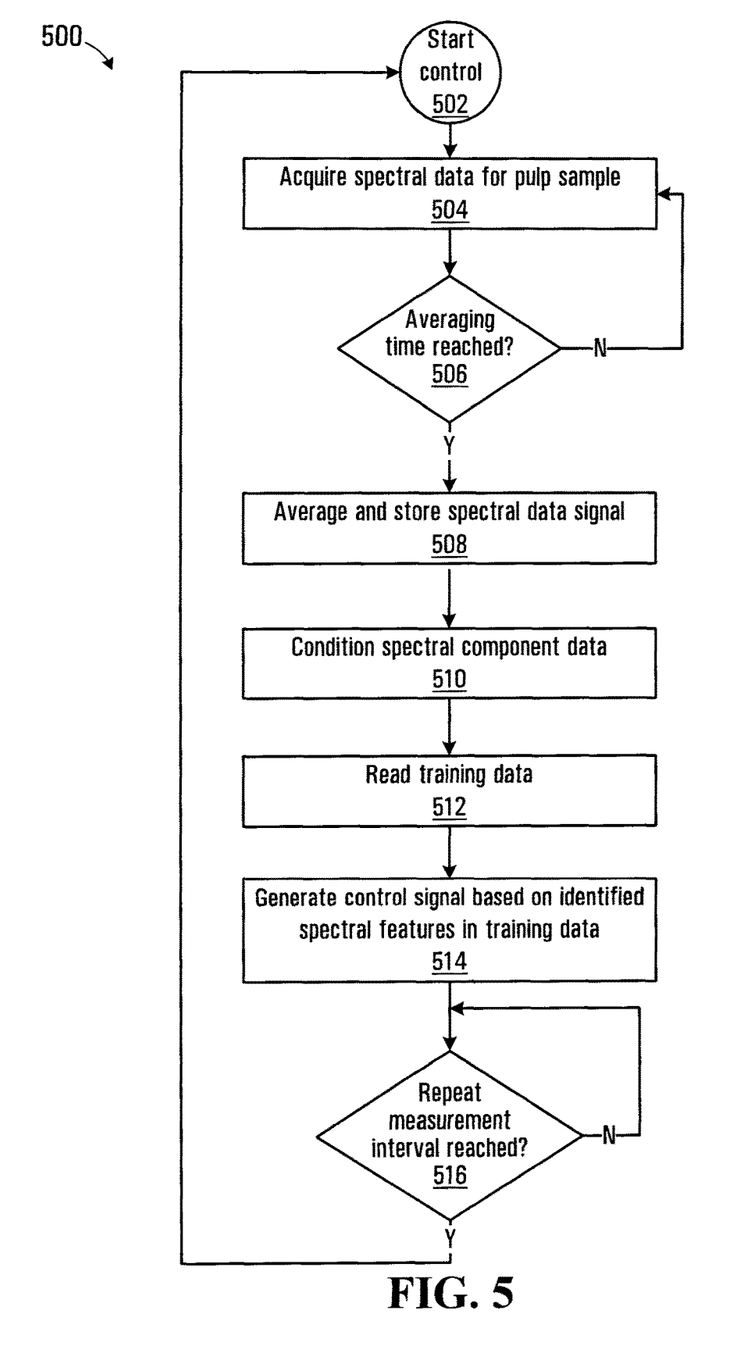
FIG. 5 is process flowchart depicting blocks of codes for directing the processor circuit to implement a control process.

Referring to FIG. 5, a process flowchart for operation of the processor circuit 230 for generating the control signal for controlling the pulp processing plant 100 to produce pulp having a desired pulp property is shown at 500. The control process 500 begins at block 502, which directs the microprocessor 300 to load and execute the pulp process control function program codes 324 from the program memory 320. Block 504 then directs the microprocessor 300 to cause the I/O 302 to acquire spectral data at the input 232 of the interface 304 for the flow of pulp material 204. Block 506 then directs the microprocessor 300 to determine whether an averaging time for the pulp sample has been reached. If at block 506 the averaging time has not yet been reached, the microprocessor 300 is directed back to block 504 and a further sample of the spectral data is acquired. If at block 506, the averaging time has been reached, the microprocessor 300 is directed to block 508, which directs the microprocessor to average and store the spectral data in the control data memory location 346 of the variable memory 340. Blocks 504 to 508 thus generally correspond to the functions performed in blocks 404-408 of the training process 400 except that the control process 500 may implement less data averaging since quicker data acquisition may be required for the control process.

Block 510 then directs the microprocessor 300 to condition the spectral data, which in this embodiment involves implementing the same discrete wavelet transform (DWT) process described above in connection with block 412 of the training process 400.

The control process then continues at block 512, which directs the microprocessor 300 to read the training data from the training data location 344 in the variable memory 340. The training data is applied to the conditioned spectral data provided by block 510 and produces a predicted value for the pulp property. Training values for the pulp property may be established using conventional pulp testing protocols and methodologies. For example, pulp handsheets may be made from the pulp and tested for strength, quality, or other properties, and the values for these properties may be used as training values.

The control signal may be used to cause the predicted value of the pulp property to be displayed on the display 350 shown in FIG. 3 for providing operator feedback. The operator may manually adjust processing parameters associated with the pulp processing plant 100 in response to the pulp property value. For example, if the pulp tensile strength is trending toward a lower value within a range of acceptable values, the bleaching time may be reduced. Alternatively, the control signal may generate a control signal for coupling to an actuator (not shown) associated with one or more stages of the pulp processing plant 100. In some embodiments, the control signal may be used to divert or direct pulp products that meet a quality criteria for specific purposes. For example, low quality product could be diverted for sale to customers who are less sensitive to pulp product quality.

Block 516 then directs the microprocessor 300 to determine whether a repeat measurement time interval has been reached. In generally the process 500 may be repeated at time intervals selected in accordance with the processing time in the pulp processing plant 100. For example, in a pulping process lasting many hours, it may only be necessary to execute the process 500 at 10 to 15 minute intervals. If at block 516 the repeat measurement interval has not yet been reached, the microprocessor 300 is directed to repeat block 516. When the repeat measurement interval is reached at block 516, the microprocessor 300 is directed back to 502 and the process is repeated.

While specific embodiments of the invention have been described and illustrated, such embodiments should be considered illustrative of the invention only and not as limiting the invention as construed in accordance with the accompanying claims.

What is claimed is:

1. A method for controlling a cellulosic pulp process for producing a pulp product having a desired pulp property, the method comprising:

illuminating an in-process portion of pulp using a first wavelength of light;

receiving a scattered light spectrum from the illuminated portion of pulp, the scattered light spectrum including spectral components that have been shifted in wavelength through interaction with a constituent of the illuminated portion of pulp;

filtering the scattered light spectrum to separate the spectral components that have been shifted in wavelength from spectral components at the first wavelength;

identifying spectral features in the filtered scattered light spectrum that correspond to the pulp property, the pulp property including at least one of a tensile strength, a viscosity, a degree of polymerization, or a hemicellulose content of the pulp produced by the pulp process; and generating a control signal for controlling the pulp process based on variations in the identified spectral features to cause the pulp property to fall within a desired range.

2. The method of claim 1 wherein generating the control signal comprises generating a display signal for controlling a display to cause information associated with the pulp property to be displayed.

3. The method of claim 1 wherein generating the control signal comprises generating a control signal operable to cause a change to a process parameter associated with the pulp process.

4. The method of claim 3 wherein generating the control signal further comprises generating a control signal based on a combination of variations in the identified spectral features and other properties of the pulp process.

5. The method of claim 1 wherein illuminating comprises illuminating the in-process portion of pulp using a laser having a wavelength of between about 532 nm and 785 nm.

6. The method of claim 1 wherein illuminating the in-process portion of pulp comprises illuminating an in-process pulp suspension.

7. The method of claim 6 wherein illuminating the in-process pulp suspension comprises illuminating a pulp suspension flowing through a conduit between processing stages of the pulp process.

8. The method of claim 6 wherein the in-process pulp suspension has a pulp consistency of between about 3% and about 6%.

9. The method of claim 6 wherein the in-process pulp suspension comprises a reduced lignin content.

10. The method of claim 1 wherein receiving the scattered light spectrum comprises:

receiving the scattered light spectrum at a diffraction grating configured to spatially disperse spectral components as a function of wavelength; and receiving the spatially dispersed spectral components at a charge coupled device (CCD) image sensor having a plurality of elements operable to provide respective intensities of the spatially dispersed spectral components.

11. The method of claim 1 wherein receiving the scattered light spectrum comprises:

receiving scattered light at a receiver operable to produce a spectral signal in response to receiving the scattered light; and generating a digital spectral representation of the spectral signal.

12. The method of claim 11 wherein identifying spectral features comprises processing the digital spectral representation to facilitate identification of the spectral features that correspond to the pulp property.

13. The method of claim 12 wherein the processing and the identifying is performed using algorithms that facilitate identification of the spectral features within a time period sufficient to facilitate control of the pulp process to produce the pulp product having the desired pulp property.

14. The method of claim 12 wherein processing comprises at least one of:

performing a first-derivative transformation on the digital spectral representation; and performing a discrete wavelength transform on the first-derivative transformation on the digital spectral representation.

15. The method of claim 1 wherein identifying comprises performing a training analysis on the processed digital spectral representation to correlate spectral components in the digital spectral representation with the pulp property.

16. The method of claim 15 wherein performing the training analysis comprises performing a training analysis prior to the identifying, and wherein identifying comprises applying results of the training analysis to the received scattered light spectrum.

17. The method of claim 1 wherein the pulp process comprises a dissolving pulp process.

18. The method of claim 17 wherein the pulp process comprises one of a kraft pulp process, and a sulfite pulp process, and a thermomechanical pulp process.

19. An apparatus for controlling a cellulosic pulp process for producing a pulp product having a desired pulp property, the apparatus comprising:

an illumination source operable to produce a first wavelength of light for illuminating an in-process portion of pulp;

a receiver operable to:

receive a scattered light spectrum from the illuminated portion of pulp, the scattered light spectrum including spectral components that have been shifted in wavelength through interaction with a constituent of the illuminated portion of pulp;

filter the scattered light spectrum to separate the spectral components that have been shifted in wavelength from spectral components at the first wavelength;

a processor circuit operably configured to:

identify spectral features in the filtered scattered light spectrum that correspond to the pulp property, the pulp property including at least one of a tensile strength, a viscosity, a degree of polymerization, and a hemicellulose content of the pulp produced by the pulp process; and generate a control signal for controlling the pulp process based on variations in the identified spectral features to cause the pulp property to fall within a desired range.

20. The apparatus of claim 19 further comprising a display and wherein generating the control signal comprises generating a display signal for controlling the display to cause information associated with the pulp property to be displayed.

21. The apparatus of claim 19 wherein the control signal comprises a signal operable to cause a change to a process parameter associated with the pulp process.

22. The apparatus of claim 19 the processor circuit is operably configured to generating the control signal by combining variations in the identified spectral features and other properties of the pulp process.

23. The apparatus of claim 19 wherein the illuminator comprises a laser having a wavelength of between about 532 nm and 785 nm.

24. The apparatus of claim 19 wherein the illuminator is operably configured to illuminate an in-process portion of pulp by illuminating an in-process pulp suspension.

25. The apparatus of claim 24 wherein the illuminator is operably configured to illuminate a pulp suspension flowing through a conduit between processing stages of the pulp process.

26. The apparatus of claim 24 wherein the in-process pulp suspension has a pulp consistency of between about 3% and about 6%.

27. The apparatus of claim 24 wherein the in-process pulp suspension comprises a reduced lignin content.

28. The apparatus of claim 19 wherein the receiver comprises:
   a diffraction grating operably configured to receive the scattered light spectrum and to spatially disperse spectral components as a function of wavelength; and
   a charge coupled device (CCD) image sensor operably configured to receive the spatially dispersed spectral components, the CCD having a plurality of elements operable to provide respective intensities of the spatially dispersed spectral components.

29. The apparatus of claim 19 wherein the receiver is operable to produce a spectral signal in response to receiving the scattered light and to generate a digital spectral representation of the spectral signal.

30. The apparatus of claim 29 wherein the processor circuit is operably configured to identify spectral features by processing the digital spectral representation to facilitate identification of the spectral features that correspond to the pulp property.

31. The apparatus of claim 30 wherein the processor circuit is operably configured to perform the processing and the identifying using algorithms that facilitate identification of the spectral features within a time period sufficient to facilitate control of the pulp process to produce the pulp product having the desired pulp property.

32. The apparatus of claim 30 wherein the processor circuit is operably configured to perform the processing by at least one of:
   performing a first-derivative transformation on the digital spectral representation; and
   performing a discrete wavelength transform on the first-derivative transformation on the digital spectral representation.

33. The apparatus of claim 19 wherein the processor circuit is operably configured to perform the identifying by performing a training analysis on the processed digital spectral representation to correlate spectral components in the digital spectral representation with the pulp property.

34. The apparatus of claim 33 wherein the processor circuit is operably configured to perform the training analysis by performing a training analysis prior to the identifying, and wherein identifying comprises applying results of the training analysis to the received scattered light spectrum.

35. The apparatus of claim 19 wherein the pulp process comprises a dissolving pulp process.

36. The apparatus of claim 35 wherein the pulp process comprises one of a kraft pulp process, a sulfite pulp process, and a thermomechanical pulp process.

* * * * *